United States Patent [19]

Harbridge et al.

[11] 4,079,177
[45] Mar. 14, 1978

[54] CLAVULANIC ACID CARBAMATES

[75] Inventors: John Barry Harbridge, Coulsdon; Thomas Trefor Howarth, Ewhurst, both of England

[73] Assignee: Beecham Group Limited, Great Britain

[21] Appl. No.: 730,192

[22] Filed: Oct. 6, 1976

[30] Foreign Application Priority Data

Oct. 13, 1975 United Kingdom ............... 41899/75

[51] Int. Cl.² ........................................... C07D 498/04
[52] U.S. Cl. ............................. 542/416; 260/307 FA; 424/246; 424/271; 424/272
[58] Field of Search .................... 260/307 FA, 240 R; 424/272; 542/416

[56] References Cited
PUBLICATIONS

Cole et al., C.A. 84, 72635t (1976).

Primary Examiner—Raymond V. Rush
Attorney, Agent, or Firm—Jacobs & Jacobs

[57] ABSTRACT

Compounds of the formula:

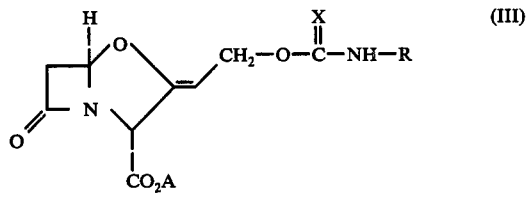

wherein X is oxygen or sulphur, R is hydrogen or an inert organic group of up to 18 carbon atoms, and A is a group such that $CO_2A$ represents a carboxylic acid group or a salt or ester thereof useful for their antibacterial activity and may be combined with a penicillin or cephalosporin to produce pharmaceutical compositions having enhanced antibacterial properties.

11 Claims, No Drawings

CLAVULANIC ACID CARBAMATES

The present invention relates to β-lactam containing compounds, to their preparation and to compositions containing them.

Belgian Pat. Nos. 827926 and 840253 disclose inter alia the compounds of the formula (I) and (II) respectively.

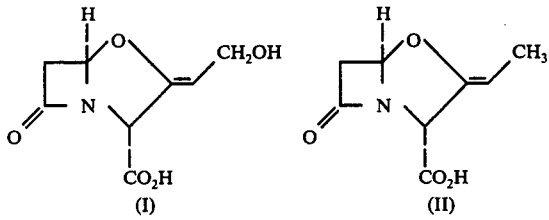

and their salts and esters.

The compounds of the formula (I) and (II) are able to inhibit β-lactamases from a range of bacteria and owing to this useful property are able to enhance the effectiveness of penicillins and cephalosporins against many gram-positive and gram-negative bacteria. It has now been discovered that certain derivatives of clavulanic acid also possess useful β-lactamase inhibitory activity and are also useful intermediates in the preparation of the compounds of the formula (II) and its salts and esters.

Accordingly the present invention provides the compounds of the formula (III):

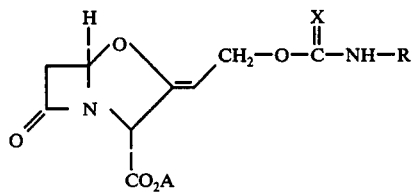

wherein X is an oxygen or sulphur atom, R is a hydrogen atom or an inert organic group of up to 18 carbon atoms and A is a group such that $CO_2A$ represents a carboxylic acid group or a salt or ester thereof.

Suitable inert organic groups R for inclusion in the compounds of formula (III) include hydrocarbon groups and hydrocarbon groups inertly substituted by halogen or by groups of the sub-formulae $—OR^1$, $—O.CO.R^1$, $—CO—R^1$, $CO_2R^1$ wherein $R^1$ is a hydrocarbon group of up to 8 carbon atoms.

Most suitably X is an oxygen atom.

Most suitably R is a hydrogen atom or in inert group of up to 14 carbon atoms.

Thus particularly suitable compounds of the formula (III) include those of the formula (IV):

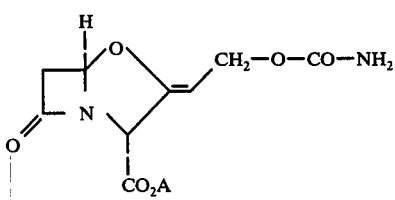

wherein A is defined in relation to formula (III); and also those of the formula (V):

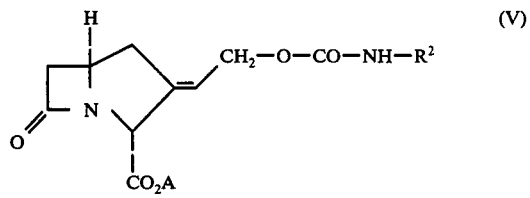

wherein $R^2$ is a group of up to 10 carbon atoms which is a hydrocarbon group or a hydrocarbon group inertly substituted by halogen or group of the formula $—OR^1$, $O—CO—R^1$, $—CO_2R^1$ wherein $R^1$ is a hydrocarbon group of up to 8 carbon atoms and A is as defined in relation to formula (III).

Most suitably the inert group $R^2$ contains up to 8 carbon atoms and is a hydrocarbon group or a hydrocarbon group substituted by halogen or a group of the sub-formulae $—OR^1$, $—O—CO—R^1$, $—CO—R^1$ or $CO_2R^1$ wherein $R^1$ is a hydrocarbon group.

Particularly suitable groups $R^2$ include methyl, ethyl, propyl, butyl, phenyl, methoxyphenyl, chlorophenyl, methylphenyl, 2-methoxy ethyl 2-acetoxyethyl, ethoxycarbonylmethyl and the like.

Preferably $R^2$ is a methyl, ethyl, propyl, butyl or phenyl group.

Particularly suitable compounds of the formulae (III), (IV) and (V) in salt form include pharmaceutically acceptable salts such as those wherein A represents a lithium, sodium, potassium, calcium, magnesium or the like ion. The sodium or potassium salts of the compounds of the formulae (III), (IV) and (V) are preferred.

The compounds of the formulae (III), (IV) and (V) wherein A is a hydrogen atom are also particularly suitable compounds of this invention.

Suitable esters of this invention include compounds of the formulae (III), (IV) and (V) wherein A is a group within the definition of R. In general the esters of this invention serve as intermediates to or pro-drugs for the acids or salts of the formulae (III), (IV) and (V).

Particularly suitable esters of this invention include those of the formulae (VI) and (VII):

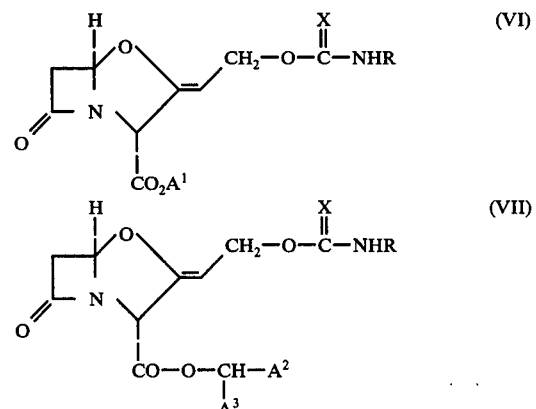

wherein X and R are as defined in relation to formula (III) and $A^1$ is an alkyl group of 1-8 carbon atoms optionally substituted by halogen or a group of the formula $OA^4$, $OCOA^4$, $SA^4$, $SO_2A^4$ wherein $A^4$ is a hydrocarbon group of up to 6 carbon atoms; $A^2$ is a hydrogen atom, an alkyl group of up to 4 carbon atoms or a phenyl group otionally substituted by halogen or by a group $A^5$ or $OA^5$ where $A^5$ is an alkyl group of up to 6 carbon atoms; and $A^3$ is a phenyl group optionally substituted by halogen or by a group $A^5$ or $OA^5$ is an alkyl group.

Preferably $A^1$ is a methyl group.
Preferably $A^2$ is a hydrogen atom.
Preferably $A^3$ is a phenyl group.

In an alternative aspect the present invention provides pharmaceutical compositions which contain a compound of the formula (III).

The compositions of the invention include those in a form adapted for oral or parental use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Unit dose compositions comprising a compound of the formula (III) or a salt or ester thereof adapted for oral administration form a further preferred composition aspect of this invention.

The compound of the formula (III) or its salts or ester may be present in the composition as sole therapeutic agent or it may be present together with another β-lactam antibiotic. Suitable β-lactam anitbiotics for inclusion in such synergistic compositions include those named in Belgian Pat. No. 827,926.

When present in a pharmaceutical composition together with a β-lactam antibiotic the ratio of a compound of the formula (III) or its salt or ester present to β-lactam antibiotic present may be from, for example, 10:1 to 1:10 and advantageously may be from 3:1 to 1:3.

The total quantity of antibacterial agents present in any unit dosage form will normally be between 50 and 1500 mg. and will usually be between 100 and 1000 mg.

Compositions of this invention may be used for the treatment of infections of inter alia the respiratory tract, the urinary tract and soft tissues in humans and mastitis in cattle.

Normally between 50 and 6000 mg of the compositions of the invention will be administered each day of treatment but more usually between 50 mgs and 300 mgs.

Particularly suitable penicillins for inclusion in the mixed compositions include amoxycillin (e.g. as the sodium salt or trihydrate) and ampicillin (e.g. as the sodium salt, anhydrate or trihydrate).

The compounds of the formula (III) as hereinbefore defined may be prepared according to this invention by the reaction of a compound of the formula (VIII):

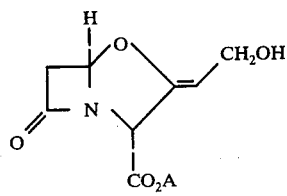

wherein A is a group such that $CO_2A$ is an esterified carboxyl group, with a compound of the formula (IX):

$$Q-N=C=X \qquad (IX)$$

wherein X is an oxygen or sulphur atom and Q is (a) a group R as defined in relation to formula (III) other than hydrogen; (b) a group $Si(N=C=X)_3$; or (c) a group $R^3R^4R^5SiNCX$ wherein $R^3$ is a methyl group or a methyl group substituted by halogen atoms or other conventional substituents; $R^4$ and $R^5$ are each a benzyl or methyl group or a methyl group substituted by halogen atoms or other conventional substituents and X is an oxygen or sulphur atom; followed if desired by the step of de-esterifying the initially produced ester to yield the free acid or salt thereof.

One particularly suitable process aspect of this invention comprises the preparation of an ester of the compound of the formula (X):

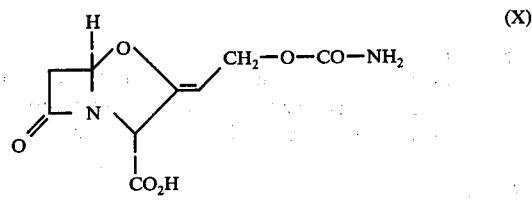

by the reaction of the corresponding ester of the compound of the formula (I) with (a) tetraisocyanatosilane or (b) a compound of the formula $(CH_3)_3SiNCO$.

A further particularly suitable process aspect of this invention comprises the preparation of an ester of the compound of the formula (XI)

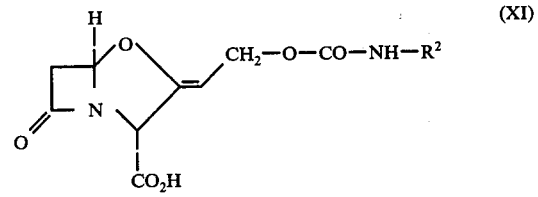

wherein $R^2$ is as defined in relation to formula (V) by the reaction of a compound of the formula (XII):

$$R^2-N=C=O \qquad (XII)$$

wherein $R^2$ is as defined in relation to formula (V) with the corresponding ester of the compound of the formula (I).

The reaction of the ester of the compound of the formula (I) with the carbamoylising agent may take place in the absence of an additional solvent if the ester is soluble in excess carbamoylising agent. If this condition does not pertain addition of an inert organic solvent is necessary. Suitable solvents include tetrahydrofuran, dioxane, dimethylformamide, methylene dichloride and the like.

Normally the carbamoylising reaction takes place at a non-extreme temperature such as $-20°$ to $+40°$ C, more suitably at from 0° to 25° C, for example at about 15° to 20° C.

The desired compound may be retrieved from the reaction mixture in conventional manner, for example by evaporation of the solvents under reduced pressure.

In a further process aspect this invention provides a process for the preparation of a compound of the formula (XIII):

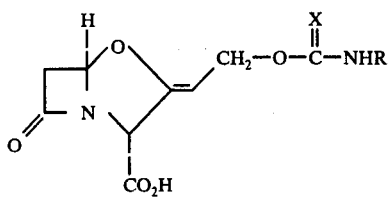 (XIII)

wherein X and R are as defined in relation to formula (III) which process comprises the hydrogenation of a solution of a corresponding ester of the formula (VII) in tetrahydrofuran.

Preparation of the acids of this invention will normally take place by hydrogenation at low or medium pressures of hydrogen, for example, at about 1 atmosphere, in the presence of a transition metal catalyst, for example, palladium on charcoal.

This invention also provides a process for the preparation of salts of the compounds of formula (XIII) which process comprises the neutralisation of the compound of the formula (XIII) with a base.

The compounds of the formula (III) serve as useful intermediates in that they may be converted into the compound of the formula (II) and its salts and esters by the hydrogenation of a compound of the formula (III) in a protic solvent in the presence of palladium.

A convenient method for preparing the compound of the formula (III) or a salt thereof is to hydrogenate a compound of the formula (VII), and in particular to hydrogenate a compound of the formula (VII) wherein $A^2$ is a hydrogen and $A^3$ is a phenyl, in a protic solvent in the presence of palladium on charcoal followed by conversion to the salts ion exchange.

Suitably the protic solvent is a $C_{1-6}$ alkanol, for example ethanol.

Suitably the hydrogenation reaction is carried out at a non-extreme temperature such as $-20°$ to $80°$ C and conveniently at room temperature and at approximately one atmosphere of hydrogen.

The palladium on charcoal will normally be present in the weight ratio of 2:1 to 1:2 of the weight of compound of the formula (III) and conveniently in the approximate ratio of 1:1.

EXAMPLE 1

Benzyl N-methylcarbamoylclavulanate

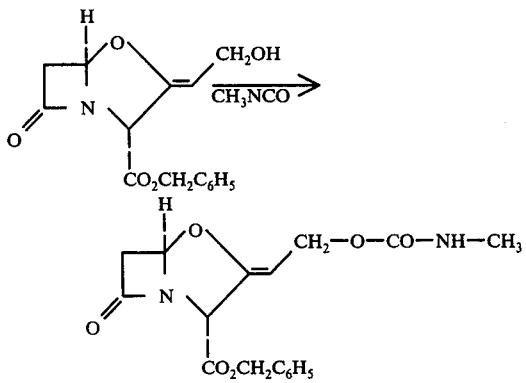

A solution of benzyl clavulanate (289 mg) in methyl isocyanate (3 ml) was allowed to stand at room temperature for 48 hours. Evaporation of the excess methyl isocyanate under reduced pressure yielded the title compound (340 mg) as a pale yellow oil.

I.r. (liquid film): γmax = 1808 (β-lactam carbonyl), 1755, 1730, 1715, 1700 (ester carbonyls and C=C), 3400 (broad: OH,NH).

n.m.r. (CDCl$_3$) 2.79 (3H,m, NHCH$_3$), 3.04(1H,dd,J 18Hz, J' 1.5Hz, 6β-CH), 3.54 (1H,dd J, 18Hz, J' 3Hz, 6α-CH, 4.5 - 5.0 (3H,m, =CHCH$_2$), 5.11 (1H,s, 3-CH), 5.22 (2H,s, OCH$_2$C$_6$H$_5$), 5.72 (1H,dd, J 3Hz J' 1.5Hz), 7.40δ (5H,s, aromatic protons).

EXAMPLE 2

N-methylcarbamoylclavulanic acid

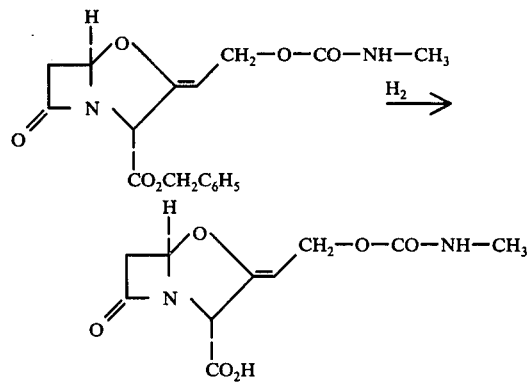

Benzyl N-methylcarbamoylclavulante (175 mg) in freshly distilled tetrahydrofuran (5 ml) was hydrogenated at ambient temperature and pressure over palladium on charcoal (10% 50 mg). When uptake of hydrogen had almost ceased (about 10 minutes) the catalyst was removed by filtration, washed with tetrahydrofuran and the filtrate and washings evaporated under reduced pressure to yield the title compound as a nearly colourless oil (pure by t.l.c.).

I.r. (liquid film): broad new adsorption γmax 2400cm$^{-1}$(COOH).

n.m.r. (CDCl$_3$) 2.75 (3H, bd, NHCH$_3$), 3.06 (1H,d, J 16Hz, 6β-C$\underline{H}$), 3.49 (1H,dd, J 16Hz J' 3Hz, 6α-CH), 4.6 - 5.1 (4H,m, =CHCH$_2$O, 3-CH), 5.71 (1H,d, J 3Hz, 5-C$\underline{H}$), 8.95δ (bs).

EXAMPLE 3

Sodium N-methylcarbamoylclavulanate

N-methylcarbamoylclavulanic acid (100 mg) was dissolved in ethanol (5 ml) and water (1 ml). To this solution was added solid sodium hydrogen carbonate (300 mg). After effervescence ceased the excess base was filtered off and the solvents evaporated under reduce pressure. The residue was dried under reduced pressure to yield the title compound.

I.r. (DMSO solution liquid film): γmax =1700 cm$^{-1}$ (β-lactam CO), 1700 cm$^{-1}$ (ester, C=C), 1630 cm$^{-1}$ (COO-).

n.m.r. (D$_2$O) 2.88 (3H,s, NCH$_3$) 3.20 (1H,d, J 18Hz, 6β-CH) 3.70 (1H,dd, J 18Hz J' 3Hz 6α-C$\underline{H}$) 5.7δ (1H,d, J 3Hz, 5-C$\underline{H}$); the other protons were obscured by the water peak. The n.m.r. solution showed signs of rapid degradation and an insoluble material was deposited.

EXAMPLE 4

Benzyl N-phenylcarbamoylclavulanate

Benzyl clavulanate (1.4 g) and isocyanatobenzene (1.7 g) were mixed and allowed to react at room temperature during 5 days. The mixture was subjected to chromatography on silica gel using ethyl acetate and petroleum ether (B.p. 40° – 60° C). The product (0.4 g) had Ir spectrum (liquid film) 3330 (NH) 1802 (β-lactam carbonyl) 1735 (broad, ester and carbonate carbonyls and C=C), 698 cm$^{-1}$ (5 adjacent protons on aromatic ring). It was a solid melting at about room temperature (22° C). The n.m.r. spectrum was consistent with the desired compound.

EXAMPLE 5

Benzyl carbamoylclavulanate

Benzyl clavulanate (0.4 g) and trimethylsilyl isocyanate (1 ml) were dissolved in the minimum quantity of dichloromethane to give one phase. The mixture was allowed to stand at room temperature for 3 days. The reaction mixture was decanted from a small amount of insoluble material and poured into a vigorously stirred dilute aqueous phosphate buffer (pH 6.8). After stirring for 30 mins, ethyl acetate (70 ml) was added, shaken, separated, the solvent layer dried over Na$_2$SO$_4$ and evaporated to a pale brown gum. TLC showed a fast-running zone still present. The material was dissolved in aqueous tetrahydrofuran, and allowed to stand until the fast-running zone had disappeared being replaced by a zone at the R$_f$ of benzyl clavulanate. The mixture was then separated by preparative high pressure liquid chromatography on silica gel using ethyl acetate as eluent. It had Ir spectrum (liquid film) 3490, 3380 (broad, NH$_2$), 1800 (β-lactam C=O), 1700 – 1760 (complex broad band, ester and carbonate C=O, and C=C). The n.m.r. spectrum was consistent with the desired product.

(The fast-running zone appears to be the trimethylsilyl ether of benzyl clavulanate).

EXAMPLE 6

Sodium deoxyclavulanate from benzyl N-methylcarbamoylclavulante

Benzyl N-methylcarbamoylclavulanate (0.15 g) and 10% palladised charcoal (0.15 g) in ethanol (7 ml) were hydrogenated. The catalyst was removed by filtration, and the filtrate evaporated. The residue was triturated with acetone (soluble) which was then evaporated to a pale brown gum. This was shown by its n.m.r. spectrum to be methylammonium deoxyclavulanate. It was dissolved in a little water, and passed down a short column of Amberlite 1R 120 cation, exchange resin in the Na$^+$ form, eluting with water. The eluate was evaporated to dryness, dissolved in acetone (1 ml) and ethyl acetate (5 ml). On evaporation to about 2 ml, the sodium salt of deoxyclavulanic acid crystallised, it was collected and dried to yield 25 mg. Its n.m.r. spectrum was characteristic of deoxyclavulanic acid.

EXAMPLE 7

Synergistical Activity of N-methylcarbamoylclavulanic Acid

The minimum inhibitory concentrations (mic) of ampicillin N-methylcarbamoylclavulanic acid, and mixtures of ampicillin and N-methylcarbamoylclavulanic acid were determined against 4 β-lactamase producing organisms. The results are shown in Table 1.

TABLE 1

MIC's (in μg/ml) of Ampicillin and N-methylcarbamoylclavulanic acid and combinations thereof against 4 β-lactamase producing organisms.

| | Organism | | | |
|---|---|---|---|---|
| | *Staphylococcus aureus* Russell | *Klebsiella aerogenes* E70 | *Escherichia coli* JT4 | *Proteus mirabilis* C889 |
| Amplicillin alone | 500 | 250 | >5000 | >500 |
| Ampicillin + 20μg/ml | 0.39 | 3.12 | 125 | 31.25 |
| 5μg/ml | 1.0 | 7.8 | >500 | >500 |
| 1μg/ml of N-methylcarbamoyl clavulanic acid | 31.25–62.5 | 15.6 | >500 | >500 |
| N-methylcarbamoyl-clavulanic acid alone | 250 | 500 | >500 | >500 |

We claim:

1. A compound of the formula (IV) or (V):

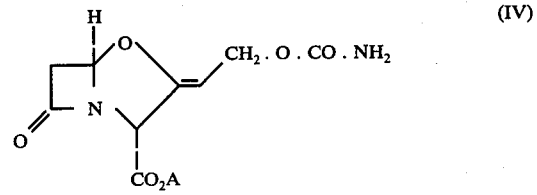

(IV)

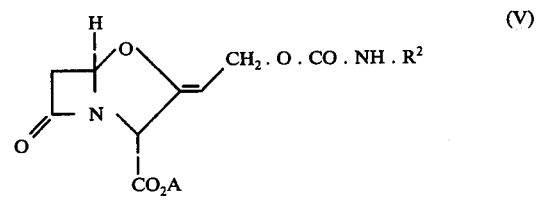

(V)

wherein R$^2$ is methyl, ethyl, propyl, butyl, phenyl, methoxyphenyl, chlorophenyl, methylphenyl, 2-methoxyethyl, 2-acetoxyethyl or ethoxycarbonylmethyl and A is a group such that CO$_2$A is a carboxylic acid group, pharmaceutically acceptable salt thereof or an ester group of the formula CO$_2$A$^1$ or CO$_2$CHA$^2$A$^3$ where A$^1$ is alkyl of 1 to 8 carbon atoms unsubstituted or substituted by halogen or a group of the formula OA$^4$, OCOA$^4$, SA$^4$ or SO$_2$A$^4$ wherein A$^4$ is a hydrocarbon group of up to 6 carbon atoms; A$^2$ is hydrogen alkyl of up to 4 carbon atoms or phenyl unsubstituted or substituted by halogen or a group A$^5$ or OA$^5$ wherein A$^5$ is alkyl of up to 6 carbon atoms; and A$^3$ is phenyl unsubstituted or substituted by halogen or by a group A$^5$ or OA$^5$ wherein A$^5$ is as above defined.

2. A compound according to claim 1 wherein A is a lithium, sodium, potassium, calcium or magnesium ion.

3. A compound according to claim 1 wherein A is hydrogen.

4. A compound according to claim 1 wherein A$^1$ is methyl.

5. A compound according to claim 1 wherein $A^2$ is hydrogen and $A^3$ is phenyl.

6. The compound according to claim 1 which is benzyl N-methylcarbamoylclavulanate.

7. The compound according to claim 1 which is N-methylcarbamoylclavulanic acid or a pharmaceutically acceptable salt thereof.

8. The compound according to claim 1 which is sodium N-methylcarbamoylclavulanate.

9. The compound according to claim 1 which is benzyl N-phenylcarbamoylclavulanate.

10. The compound according to claim 1 which is benzyl carbamoylclavulanate.

11. A compound according to claim 1 wherein $R^2$ is methyl, ethyl, propyl, butyl or phenyl.

* * * * *